(12) United States Patent
Kodama et al.

(10) Patent No.: US 7,276,691 B2
(45) Date of Patent: Oct. 2, 2007

(54) ION BEAM DEVICE AND ION BEAM PROCESSING METHOD

(75) Inventors: Toshio Kodama, Chiba (JP); Masakatsu Hasuda, Chiba (JP); Toshiaki Fujii, Chiba (JP); Kouji Iwasaki, Chiba (JP); Yasuhiko Sugiyama, Chiba (JP); Yasuyuki Takagi, Chiba (JP)

(73) Assignee: SII NanoTechnology Inc. (JP)

( * ) Notice: Subject to any disclaimer, the term of this patent is extended or adjusted under 35 U.S.C. 154(b) by 2 days.

(21) Appl. No.: 10/525,311

(22) PCT Filed: Aug. 20, 2003

(86) PCT No.: PCT/JP03/10482

§ 371 (c)(1),
(2), (4) Date: Apr. 18, 2005

(65) Prior Publication Data

US 2006/0163497 A1    Jul. 27, 2006

(30) Foreign Application Priority Data

Aug. 23, 2002 (JP) .............................. 2002-243210

(51) Int. Cl.
*H01J 37/30* (2006.01)

(52) U.S. Cl. .................................. 250/309; 250/492.21
(58) Field of Classification Search ........... 250/492.21, 250/309, 307, 310, 311, 492.2, 492.3
See application file for complete search history.

(56) References Cited

U.S. PATENT DOCUMENTS

| 5,525,806 | A | * | 6/1996 | Iwasaki et al. | ......... | 250/492.21 |
| 5,574,280 | A | * | 11/1996 | Fujii et al. | ................... | 250/309 |
| 6,838,685 | B1 | * | 1/2005 | Kodama et al. | ........ | 250/492.21 |
| 2002/0017619 | A1 | | 2/2002 | Hirose et al. | | |
| 2005/0236587 | A1 | * | 10/2005 | Kodama et al. | ........ | 250/492.21 |

FOREIGN PATENT DOCUMENTS

JP        2001 345360 A        12/2001

* cited by examiner

*Primary Examiner*—Kiet T. Nguyen
(74) *Attorney, Agent, or Firm*—Adams & Wilks (57) ABSTRACT

There is provided a liquid metal ion beam irradiation device for irradiating a specific portion of a sample 6 with a prescribed liquid metal ion beam so as to form a cross section, and a gaseous ion beam irradiation device 7 for scanning a prescribed region (observation region) of the cross section using a gaseous ion beam focused to a prescribed diameter and removing a damaged layer on the prescribed region.

19 Claims, 11 Drawing Sheets

ION BEAM DEVICE AND ION BEAM PROCESSING METHOD

CROSS REFERENCE TO RELATED APPLICATIONS

The present application is a U.S. national stage application of copending International Application No. PCT/JP2003/010482, filed Aug. 20, 2003, claiming a priority date of Aug. 23, 2002, and published in a non-English language.

FIELD OF THE INVENTION

The present invention relates to a ion beam device and ion beam processing method for irradiating and processing specific locations of a sample.

BACKGROUND ART

As an ion beam device, a focused ion beam device and an ion milling device are known. These devices are used in sample manufacture when carrying out slice observation of fault locations of a wafer using a TEM (Transmission Electron Microscope), or SEM (Scanning Electron Microscope) for example. In particular, since an FIB device scans a sample surface with a sufficiently focused ion beam and can perform accurate slice processing of specific sites such as defects while detecting secondary electrons generated at the time of scanning and observing as an image, FIB devices are widely used as evaluation devices for semiconductor manufacturing processes.

Figure 6:
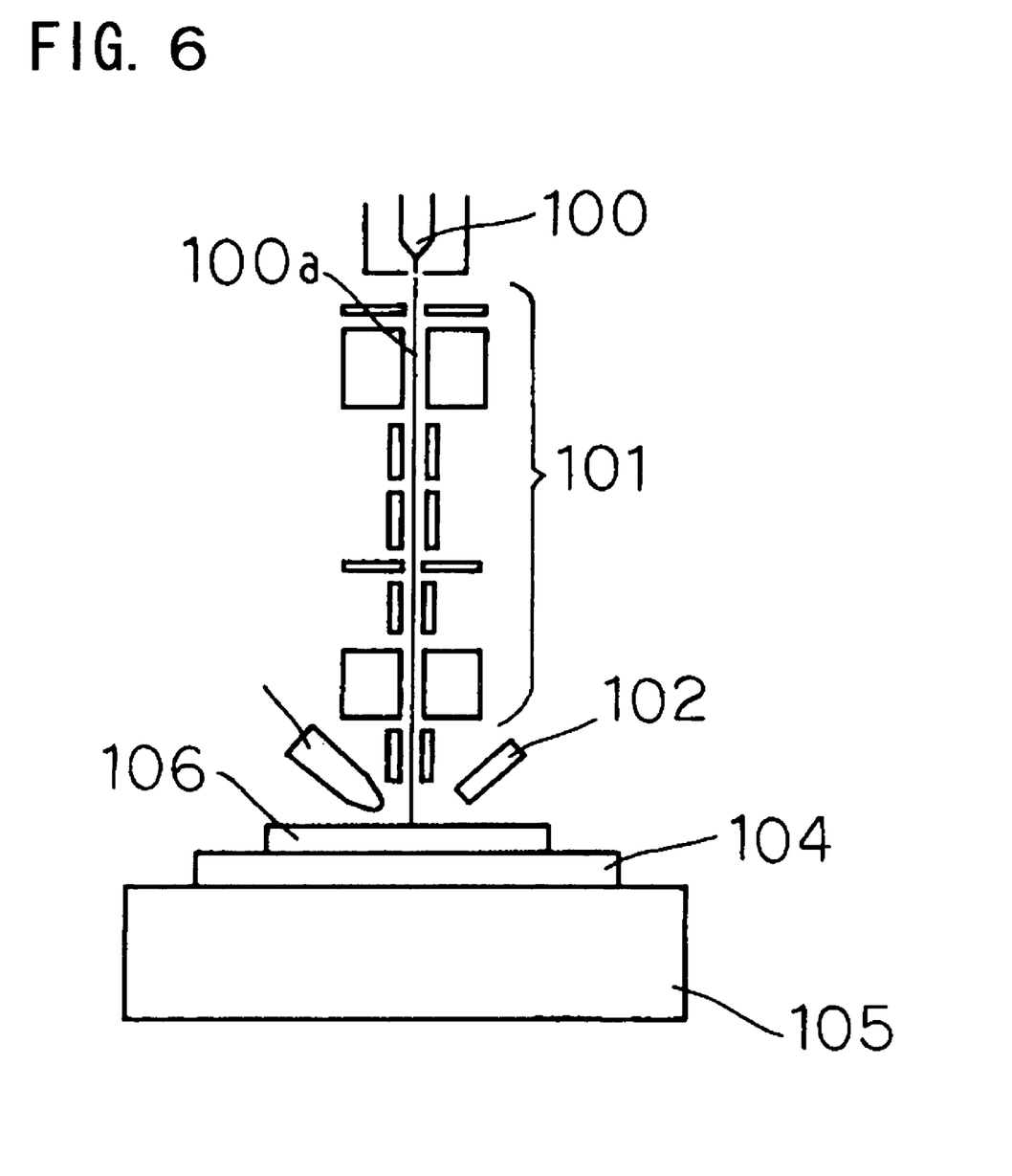
FIG. 6 is a schematic view showing an outline of a configuration for an FIB device of the related art.

The schematic structure of a conventional FIB device is shown in FIG. 6. The main parts of this FIB device are an ion source 100, an ion optical system 101, a secondary charged particle detector 102, a gas gun 103, a sample holder 104 and a sample stage 105.

The ion source 100 is a liquid metal ion source exemplified by Gallium (Ga), for example. The ion optical system 101 is for focusing an ion beam from the ion source 100, as well as scanning the ion beam on the sample 106, and has a condenser lens (electrostatic lens), beam blanker, movable aperture, 8-pole stigmeter, objective lens (electrostatic lens) and scanning electrodes etc. arranged in order from the side of the ion source 100. The secondary charged particle detector 102 is for detecting secondary charged particles generated when a sample 106 is scanned by a focused ion beam (hereinafter simply referred to as FIB) 100a. It is then possible to obtain an observed image (SIM image) using a Scanning Ion Microscope (SIM) by carrying out image processing based on these detection results.

The sample stage 105 can be controlled along five axes. With five axes of control, it is possible to control three dimensional movement in the XYZ directions, rotation around an axis (Z-axis) perpendicular to the XY plane, and tilt. The sample holder 104 is for fixing the sample 106, and the sample is conveyed on the sample stage 105 mounted on a moving platform called a boat (not shown in the drawings). The sample 106 is, for example, a wafer. A gas gun 103 is for blowing a prescribed gas for forming a deposition film as a protective layer on the surface of the sample 106.

Next, a description will be given of the basic sample manufacturing sequence that uses the above described FIB device. A series of procedures for manufacturing a TEN sample using a method referred to as a "pick up" method (or lift out method) are shown schematically in FIG. 7(a) and FIG. 7(b). In the following, the manufacturing sequence for a TEM sample will be described with reference to FIG. 6 and FIG. 7.

First, a wafer constituted by a sample 106 is fixed on the sample stage 105. Coarse positioning is then carried out in such a manner that an FIB 100a from an ion source 100 is irradiated in the vicinity of this defect location based on position information for the defect location provided in advance. Next, the vicinity of the defect location is scanned by the FIB 100a, and the position of the defect location is specified (position outputted) while looking at an SIM image obtained by this scan. After detecting the position, prescribed gas is blown onto the surface of the wafer by the gas gun 103, and a deposition film (protective film) is formed by scanning a prescribed range including the defect location of the surface of the wafer using the FIB 100a. Forming of this deposition film is typically referred to as ion assist deposition (or ion beam CVD (Chemical Vapor Deposition)) and a deposition film can be selectively formed at a portion irradiated by the FIB 100a.

Continuing on, as shown in FIG. 7(a), the vicinity of the defect portion of the wafer surface is irradiated by the FIB 100a so as to be coarsely processed, and the processed portion is irradiated with the FIB 100a so as to be subjected to finishing processing. In this processing, the FIB 100a is irradiated from a normal direction with respect to the surface of the wafer, the surface of a region irradiated by the FIB is gradually removed, and finally the cross section 107a shown in FIG. 7(b) is obtained. The extent to which the thickness of the cross-section 107a as viewed from above can be made thin changes depending on the material of the sample and the acceleration voltage of the TEM used. For example, it is necessary to make this thickness 0.1 μm or less in the case of observing a lattice image of an Si group semiconductor sample using a TEM of an acceleration voltage of 200 k. Further, in the event that 3D analysis etc. is carried out by tomography using a TEM, thickness of the sample can by finished to the order of 0.5 μm.

Finally, after the angle of incidence to the wafer of the FIB100a is adjusted by controlling the tilt angle of the sample stage 105, by processing using the FIB100a, a notch 107b (portion shown by the broken line in FIG. 7(b)) as shown in FIG. 7(b) is formed at the periphery of the portion where the cross-section 107a is formed. A portion taken out along the notch 107b containing the cross section 107a is constituted by the TEM sample 107.

Figure 8:
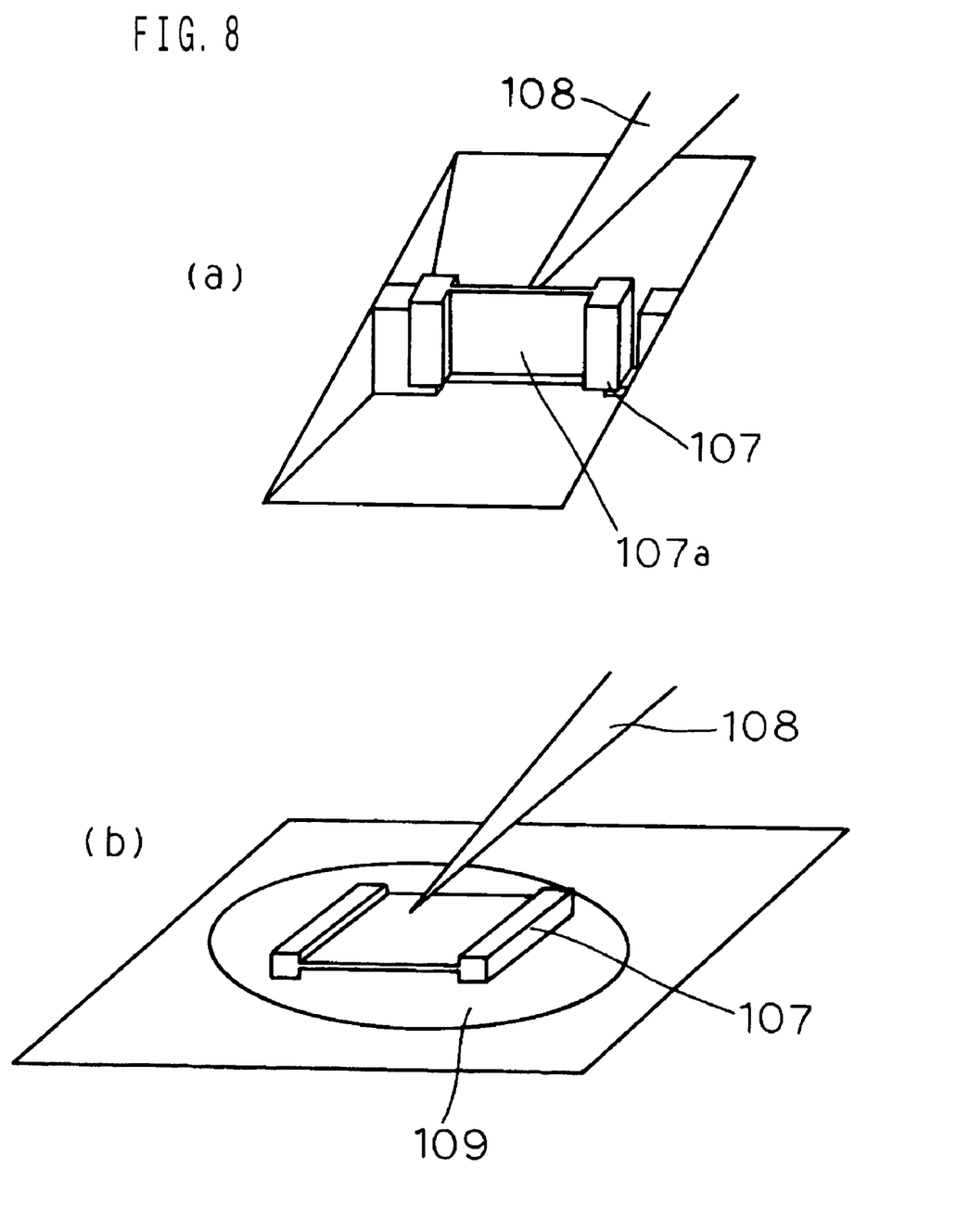
FIG. 8(a) and FIG. 8(b) are schematic views for illustrating extracting of a TEM sample using a pick-up method.

A dedicated device (manipulator) is used to take out the TEM sample 107. FIGS. 8(a) and (b) show an example of taking out the TEM sample using the pick-up method.

Figure 7:
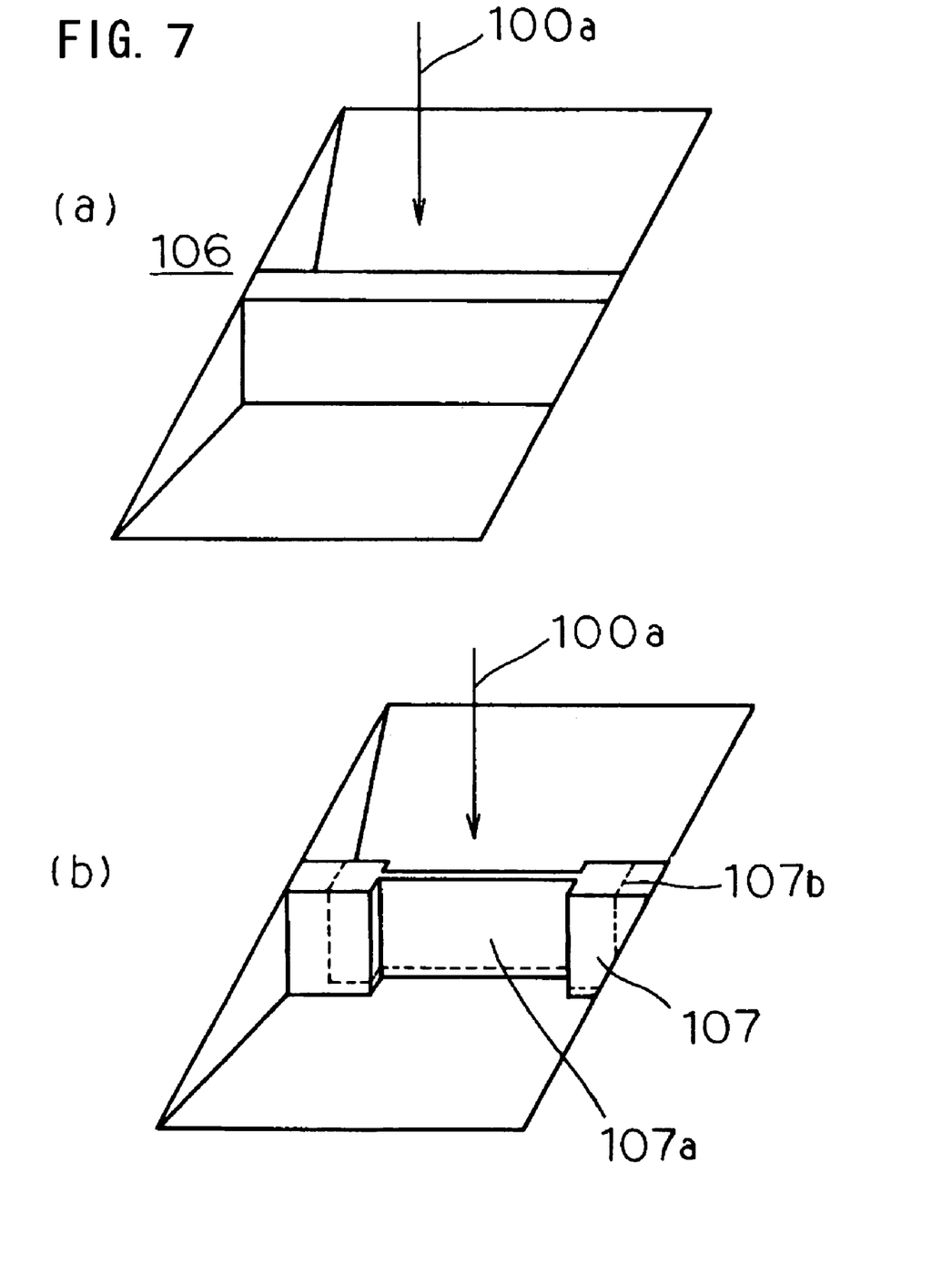
FIG. 7(a) and FIG. 7(b) are schematic views for illustrating making of a TEM sample using a pick-up method.

First, the tip of a probe 108 made of glass approaches the cross section 107a of one side of the TEM sample 107 made by the procedure of FIG. 7. When the tip of the probe 108 comes close to the cross section 107a to a certain extent, as shown in FIG. 8(a), the TEM sample 107 becomes stuck by electrostatic to the tip of the probe 108. The probe 108 is then moved to above an organic film 109 having viscosity prepared separately with the TEM sample 107 remaining in a state of being fixed to the tip, and as shown in FIG. 8(b), the TEM sample 107 stuck to the tip is placed on the organic film 109. The TEM sample 107 is fixed by the viscosity of the organic thin film 109 and is taken away from the tip of the probe 108.

The organic thin film 109 to which the TEM sample 107 is fixed is then carried to another TEM device separate from the FIB device, and observation of the cross section 107a of the TEM sample 107 is carried out. Recently, composite FIB devices incorporating observation devices such as scanning electron microscopes and energy distributed X-ray detectors etc. and manipulators etc. in an FIB device have also been proposed, with observation from sample manufacture being carried out using a single FIB device.

In addition to the methods of manufacturing a TEM sample using a pick-up method described above, methods also exist for making TEM samples by making a small sample for a specific location by splitting up a wafer using a dicing saw, fixing this small sample to a dedicated sample holder and carrying out crosssectional processing.

Figure 9:
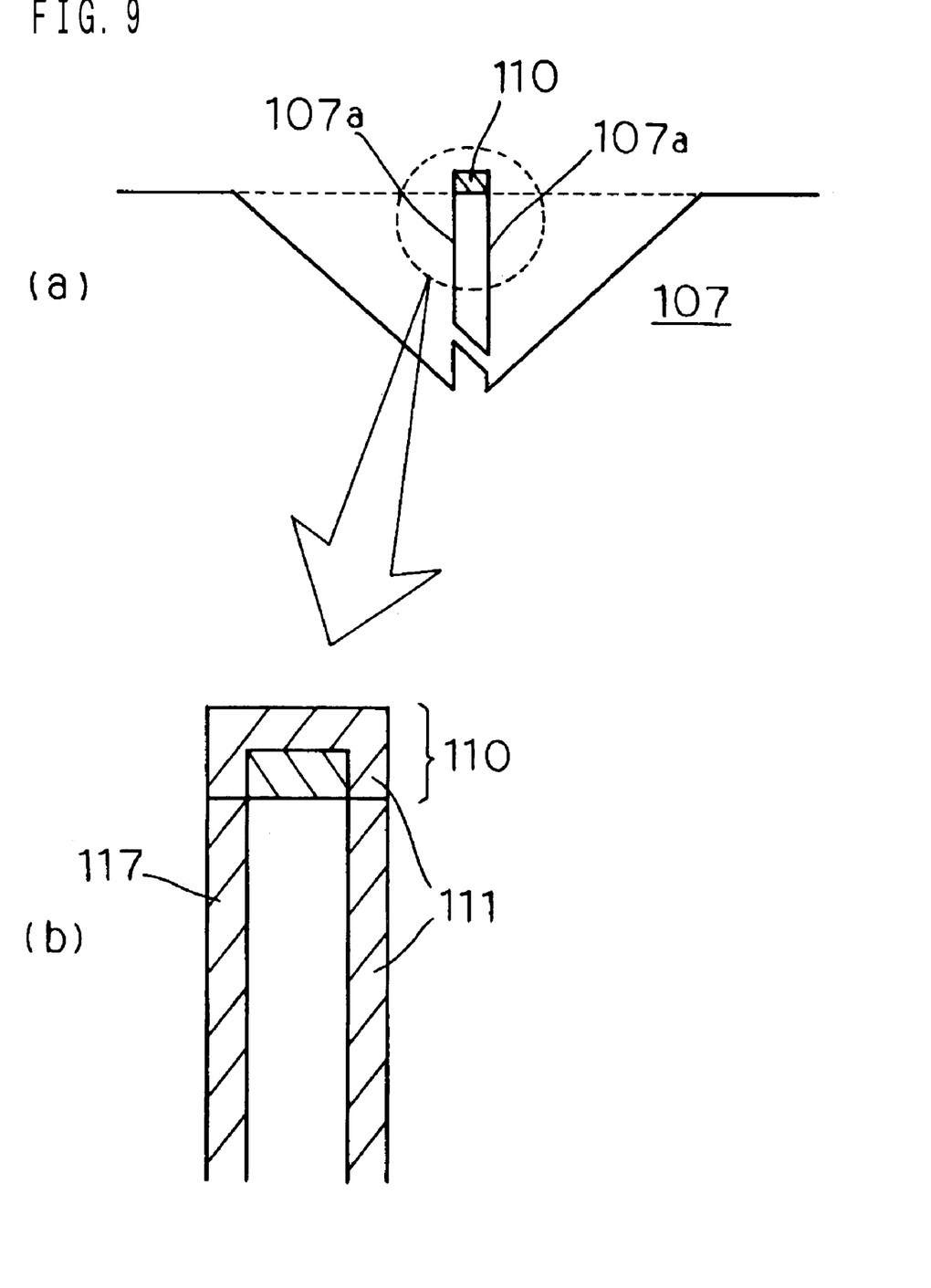
FIG. 9(a) is a cross-sectional view of a portion of the TEM sample shown in FIG. 7(b)
FIG. 9(b) is a partial enlarged view of FIG. 9(a).

However, in either of the methods for manufacturing described above, the processing surface (cross section) is subjected to damage by the FIB during cross-sectional processing by the FIB. FIG. 9(a) is a cross-sectional view of a portion of the TEM sample 107 of FIG. 7(b), and FIG. 9(b) is a partial enlarged view thereof. In FIG. 9, the deposition film 110 is a protective film formed at the time of cross section processing by the FIB.

In cross sectional processing using an FIB, damage is incurred by the surface of the cross section 107a of the TEM sample 107 and part of the ions contained in the FIB are injected so that a damaged layer (fragmented layer) 111 is formed as shown in FIG. 9(b). The damage layer 111 has an amorphous state with a mixture of elements originally included in the sample itself and injected ions (Ga). If the unwanted damage layer 111 is formed on the surface to be observed (cross section 107a) in this way, the damage layer proves a hindrance and it is not possible to carry out TEM observation, and in particular, clear lattice image observations, in a satisfactory manner. This kind of damage layer problem also similarly occurs in SEM sample manufacture.

A method of removing the damage layer by etching (ion milling) using a low energy ion beam, for example, an argon (Ar) ion beam has been proposed. For example, in Japanese Patent publication No. 3117836 (Japanese Patent Laid-open No. Hei. 6-260129), there is disclosed an FIB device capable of removing a damage layer, having a built-in ion milling device.

Figure 10:
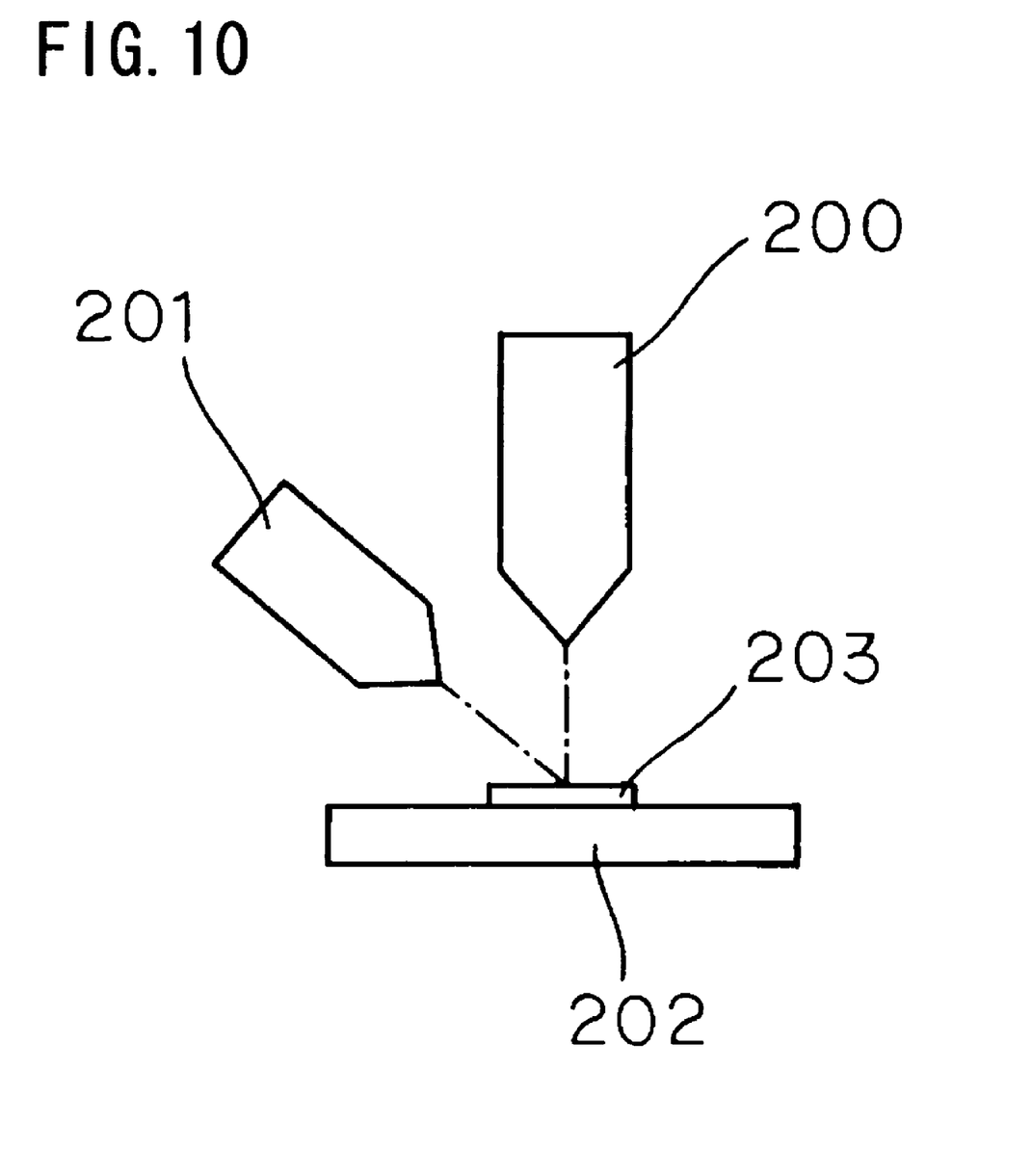
FIG. 10 is a schematic view showing an outline of the structure of an FIB device disclosed in Japanese patent laid-open publication no. Hei. 6-260129.

FIG. 10 is a schematic view showing an outline of the structure of an FIB device disclosed in the above publication. The main elements of this FIB device are a liquid metal ion beam irradiation device 200, a gas ion beam irradiation device 201, and a sample stage 202.

The liquid metal ion beam irradiation device 200, is equipped with an ion optical system as shown in FIG. 6, and is capable of scanning specified parts of the surface of the sample 203 mounted on the sample stage 202 using a sufficiently focused ion beam (FIB) drawn out from a liquid metal ion source. The liquid metal ion source is, for example a Ga ion source.

The gas ion beam irradiation device 201 uniformly irradiates a region of a prescribed range including a section that has been sliced with a gas ion beam drawn out from a gas ion source. The gaseous ion source may be, for example, an Ar ion source. A gaseous ion beam is not necessary for convergence as with an FIB. It is therefore not possible to provide an ion optical system that sufficiently converges an ion beam such as that provided in a liquid metal ion beam irradiation device 200 in a gaseous ion beam irradiation device 201. An ion optical system for sufficiently converging an ion beam is extremely expensive and a low cost is achieved by not using this.

With the above described FIB device, first of all, the sample 203 is subjected to slice processing with an FIB from the liquid metal ion beam irradiation device 200. The damaged layer is formed with the cross section shown in FIG. 9(b) during cross section processing. After slice processing, a region containing the slices section is irradiated, and the damage layer on the slice is similarly removed by etching.

There is also damage to the slice caused by the gas ion beam irradiation, but only to a small extent. The thickness of a damaged layer in the case of a gaseous ion beam is of the order of a number of nm whereas the thickness of a damaged layer is 20 to 30 nm in the case of a liquid metal ion beam. This damaged layer is therefore not a problem in observation of cross sections using a TEM or SEM.

As described above, in the case of slicing processing using a FIB, since it is possible to have a damage layer on the processed slice, there is a problem in that it is not possible to carry out favorable slice observation for a TEM or SEM etc.

By removing the damage layer after slice processing with the FIB using the gas ion beam, the above described problem is solved, but in this case, a new problem arises with regard to re-attachment of secondary particles due to irradiation with a gaseous ion beam, as will be described in the following.

Figure 11:
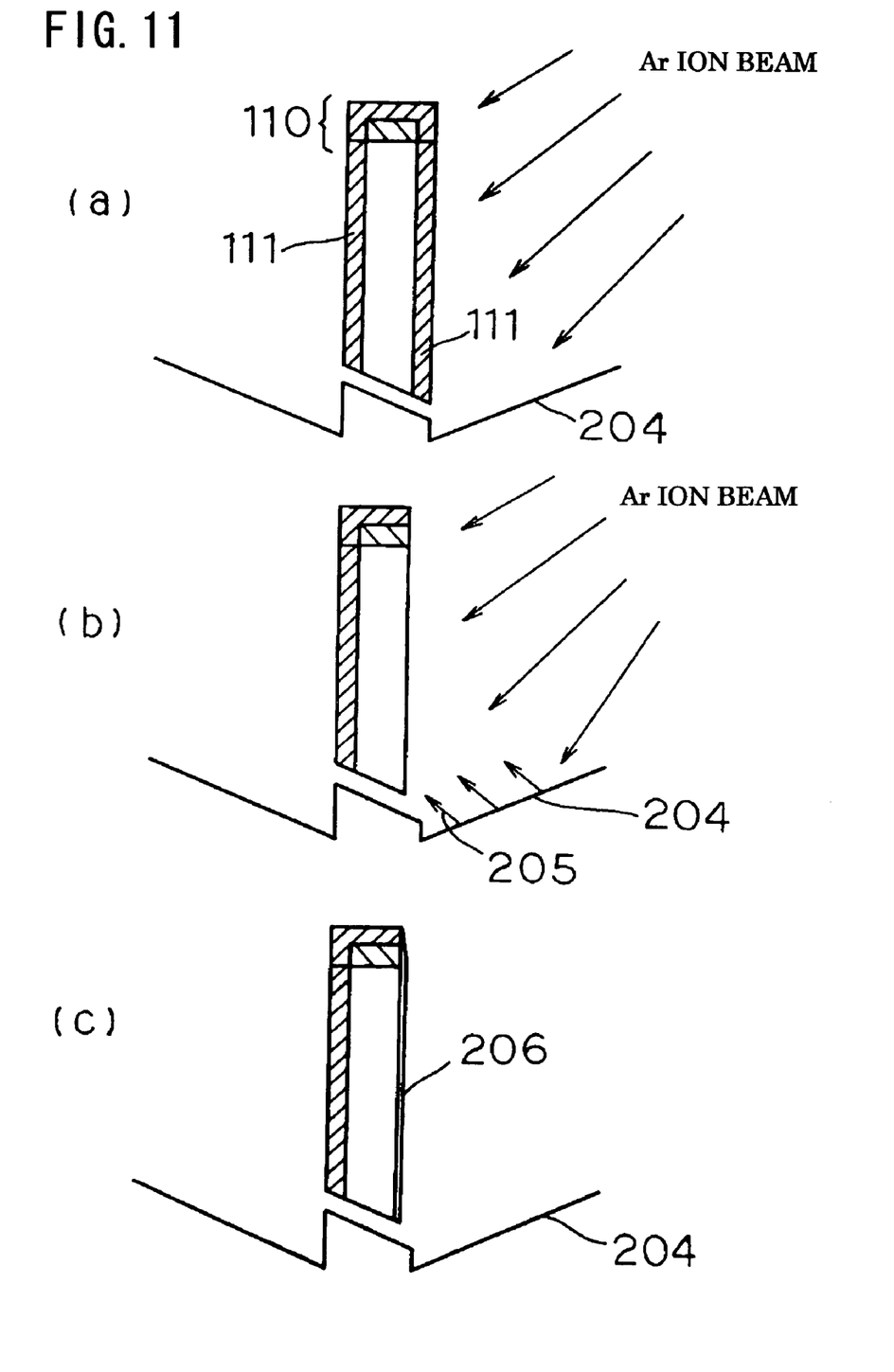

The process where the secondary particles become reattached is shown schematically in FIG. 11(a) to FIG. 11(c). As shown in FIG. 11(a), an Ar ion beam is irradiated in order to remove the damage layer 111 formed on the slice. The irradiation range of the Ar ion beam includes an adjacent surface 204 adjoining the slice. If the Ar ion beam is irradiated to the adjacent surface 204, then secondary particles 205 are ejected from the adjacent surface 204, as shown in FIG. 11(b). Secondary particles 205 ejected from this adjacent surface 204 are attached to the slice after the damage layer 111 has been removed, forming the re-attachment layer 206 as shown in FIG. 11(c). The components of the reattachment layer 206 are ambiguous and hinder effective cross section observation.

The object of the present invention is to solve the above described problems, and to provide an ion beam device and ion beam processing method capable of preventing re-attachment of secondary particles to a surface of observation (cross section).

SUMMARY OF THE INVENTION

In order to achieve the aforementioned object, the ion beam device of the present invention comprises liquid metal ion beam irradiation means for irradiating a specific portion of a sample with a prescribed liquid metal ion beam so as to form a cross section, and gaseous ion beam irradiation means for scanning a prescribed region of the cross section using a gaseous ion beam focused to a prescribed diameter and removing a damaged layer on the prescribed region.

An ion beam processing method of the present invention also comprises a first step of irradiating a specific portion of a sample with a prescribed liquid metal ion beam so as to form a cross section and a second step of scanning a prescribed region of the cross section using a gaseous ion beam focused to a prescribed diameter and removing a damaged layer on the prescribed region.

In the present invention as described above, it is possible to eliminate a damaged layer from on a prescribed region of a cross section formed as a result of irradiation with a prescribed liquid metal ion beam, specifically, an observation region subjected to SEM observation or TEM observation by scanning the region with a focused gaseous ion beam of a prescribed beam diameter. The side wall surface and bottom surface are next to each other at the cross section but these neighboring surfaces do not neighbor the observation region. Further, it is possible to limit the irradiation range of the gaseous ion beam to the observation region by focusing the gaseous ion beam to a prescribed beam diameter. As a result, in the present invention, the gaseous ion beam is only irradiated basically on the observation region and is not irradiated to the neighboring surface (side surface and bottom surface). Accordingly, the problem that occurred in the related art where neighboring surfaces become irradiated with a gaseous ion beam so that secondary particles are emitted, with the emitted secondary particles then becoming reattached to an observation region so as to become a damaged layer to be removed does not occur.

BRIEF DESCRIPTION OF THE DRAWINGS

FIG. 3(a) to FIG. 3(c) are schematic views showing a process for eliminating a damaged layer using a focused gaseous ion beam.

FIG. 4(a) to FIG. 4(d) are schematic views showing a process for making a TEM sample from a small sample.

An outline of a configuration for a composite device where a function enabling cross section observation by an SEM is incorporated in the FIB device shown in FIG. 1 is shown in FIG. 5.

FIG. 11(a) to FIG. 11(c) are schematic views showing a process forming a reattachment layer.

DETAILED DESCRIPTION OF THE INVENTION

Next, embodiments of the present invention will be described with reference to the drawings A principal structure of an FIB device, being one embodiment of the ion beam device of the present invention, is shown schematically in FIG. 1. This FIB device is comprised of a liquid metal ion beam irradiation device 1, a secondary charged particle detector 2, a gas gun 3, a sample holder 4 for fixing a sample 6, a sample stage 5, and a gaseous ion beam irradiation device 7.

The liquid metal ion beam irradiation device 1 is an existing device equipped with a liquid metal ion source and an ion optical system capable of sufficiently focusing a liquid metal ion beam drawn out from the liquid metal ion source so as to scan the sample 6. The ion optical system is the same as the ion optical system 101 shown in FIG. 6, with a condenser lens (electrostatic lens), beam blanker, moveable aperture, eight pole stigmeter, object lens (electrostatic lens), and scanning electrode etc. arranged in order from the liquid metal ion source side. For example, gallium (Ga) may be used as the liquid metal ion species.

The gaseous ion beam irradiation device 7 is equipped with a gaseous ion source and an ion optical system capable of sufficiently focusing a gaseous ion beam drawn out from the gaseous ion source so as to scan the sample 6. The ion optical system is substantially the same as the ion optical system used in the metal ion beam irradiation device 1. Argon, oxygen, helium, neon, xenon, krypton, radon etc. may be taken to be the gas ion species. The optical axis of the gaseous ion beam irradiation device 7 crosses the optical axis of the liquid metal ion beam irradiation device 1 at a prescribed position.

The gas gun 3, sample holder 4 and sample stage 5 as the same as that shown in FIG. 6. The secondary charged particle detector 2 is for detecting secondary charged particles generated while irradiating the sample 6 with a liquid metal ion beam and a gaseous ion beam. Respective SIM images for the time of etching processing using a liquid metal ion beam and the time of etching elimination using a gaseous ion beam are obtained by carrying out image processing based on these detection results.

Next, a detailed description of sample manufacture employing an FIB device of this embodiment is described. In the following description, specific descriptions are given of examples of two manufacturing procedures, a procedure for manufacturing a TEM sample using a pick-up method, and a procedure for manufacturing a TEM sample from a small piece sample made using a dicing saw.

(1) Procedure for manufacturing a TEM sample using a pick-up method.

First, the vicinity of specific locations (defect locations) of a wafer constituted by the sample 6 are scanned using a liquid metal ion beam focused from the liquid metal ion beam irradiation device 1 liquid metal ion beam irradiation device 1, and a cross section is formed (cross section processing). This cross-section processing is basically the same as shown in FIG. 7(a) and FIG. 7(b), and a detailed description thereof is omitted.

After cross section processing (processing of FIG. 7(b)), a prescribed region (observation region) of the cross section of the sample 6 is scanned using a focused gaseous ion beam from the gaseous ion beam irradiation device 7 and a damaged layer (not shown) on this prescribed region is eliminated. A schematic view showing irradiation of a cross section by a gaseous ion beam is shown in FIG. 2.

Figure 2:
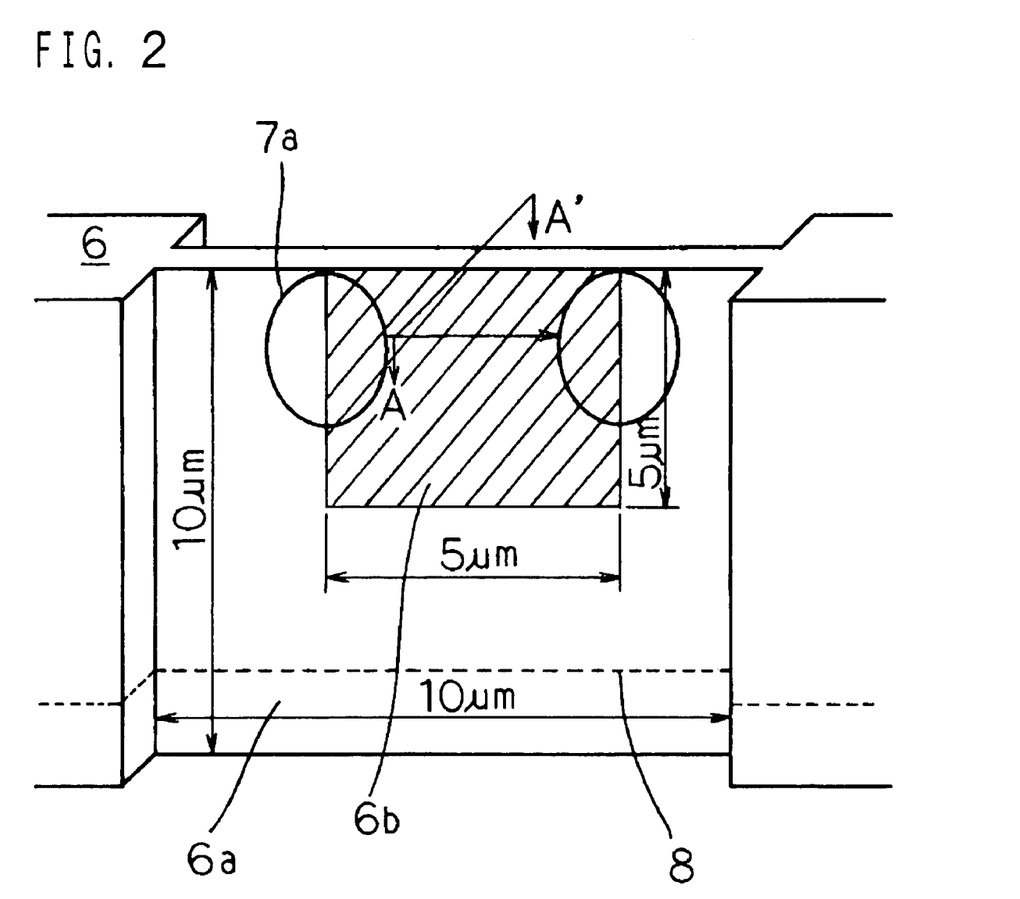
FIG. 2 is a schematic view showing irradiation of a cross section by a gaseous ion beam.

In FIG. 2, the cross section 6a is the portion processed using a focused liquid metal ion beam from the liquid metal ion beam irradiation device 1 that is a specific location of the wafer constituted by the sample 6 and is, for example, 10 μm (high(deep))×10 μm (wide)). An observation region 6b (oblique line portion shown by dashed lines) positioned at the center of this cross section is a region for which TEM observation is carried out, and is of a size of, for example, 5 μm (high (deep)×5 μm (wide)). A notch 8 (dashed lines) corresponding to the notch 107b shown in FIG. 7(b) is formed at the lower part (bottom part) of the cross section 6a, and a portion punctuated by this notch 8 is extracted as the TEM sample.

A focused gaseous ion beam from the gaseous ion beam irradiation device 7 is irradiated at an incline with respect to the cross section 6a. The size of a beam spot 7a is smaller than the size of the cross section 6a and is preferably smaller than the observation region 6b. Specifically, in the event that the size of the observation region 6b is 5 μm (high (deep))×5 μm (width)), the beam diameter (provided as half-width occurring in a gaussian distribution) on the cross section 6a is preferably in the order of a diameter of 3 μm. A damaged layer on the observation region 6b is eliminated by scanning the observation region 6b using a beam spot 7a.

FIG. 3(a) to FIG. 3(c) schematically show a process for eliminating a damaged layer using a focused gaseous ion beam. FIG. 3(a) to FIG. 3(c) correspond to the cross section A-A of the cross section 6a shown in FIG. 2.

In FIG. 3(a), a deposition film 10 is a protective film formed during cross section processing using a focused liquid metal ion beam from the liquid metal ion beam irradiation device 1. A damaged layer 11 is formed on the cross section 6a. A portion of the damaged layer 11 on the observation region 6b is scanned using a focused gaseous ion beam (beam diameter 3 μm) from the gaseous ion beam irradiation device 7 and is eliminated by etching (refer to FIG. 3(b) and FIG. 3(c)). Similar processing is then carried out for the surface on the opposite side. Irradiation of a gaseous ion beam to the surface on the opposite side can be carried out by rotating the sample stage 5 through 180 degrees.

The gaseous ion beam does not irradiate the neighboring surface 6c neighboring the cross section 6a while eliminating the damaged layer 11 because only the observation region 6b is irradiated with the focused gaseous ion beam so as to eliminate the damaged layer 11 in the aforementioned elimination by etching. Because of this, at the neighboring surface 6c, emission of secondary particles due to irradiation with a gaseous ion beam as in the related art does not occur. Accordingly, forming of a reattachment layer due to secondary particles from the neighboring surface 6c as in the related art at the surface of the observation region 6b for which the damaged layer 11 is deleted does not occur.

In the above, a TEM sample section that has been subjected to cross section processing in the above manner so as to have a damaged layer removed is extracted from the wafer using the same method as for extracting the TEM sample using a probe shown in FIG. 8(a) and FIG. 8(b) and is fixed by adhesion to an organic thin film.

Figure 3:
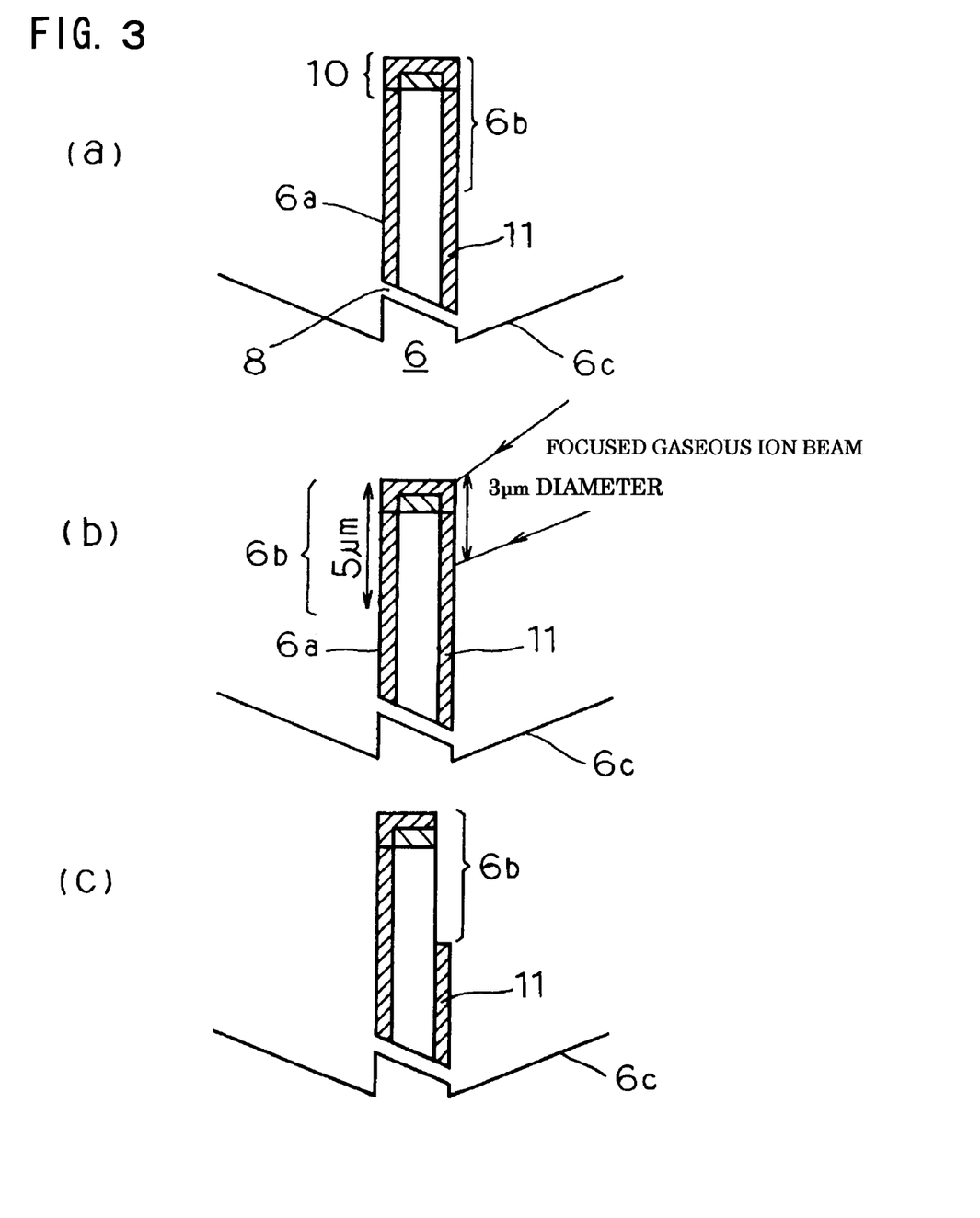

In the example in FIG. 3, only the neighboring surface 6c positioned at the lower part (bottom part) of the cross section 6a is shown as the neighboring surface but in reality, as shown in FIG. 2, neighboring surfaces exist on both sides of the cross section 6a. Gaseous ion beams are also not irradiated at these neighboring surfaces during elimination of the damaged layer using a gaseous ion beam in this embodiment.

Further, the extracted TEM sample section may also be fixed to a dedicated sample holder rather than being fixed through adhesion to an organic thin film. In this event, reprocessing of the TEM sample section is possible.

Further, if the spot size, occurring on a cross section 6a, of the focused gaseous ion beam is set to be larger (but smaller than the cross section 6a), it is possible to eliminate the damaged layer in a shorter period of time. In this event, part of the gaseous ion beam irradiates the neighboring surface and secondary particles are emitted but the extent of these emissions is quite small compared to the extent of emissions of secondary particles in the related art. As a result, even if a reattachment layer is formed at the observation region for which the damaged layer is eliminated, this amount (thickness) is only slight and cross section observation is therefore not impeded.

(2) Procedure for making a TEM sample from a small sample.

FIG. 4(a) to FIG. 4(d) show a process for making a TEM sample from a small sample.

Figure 4:
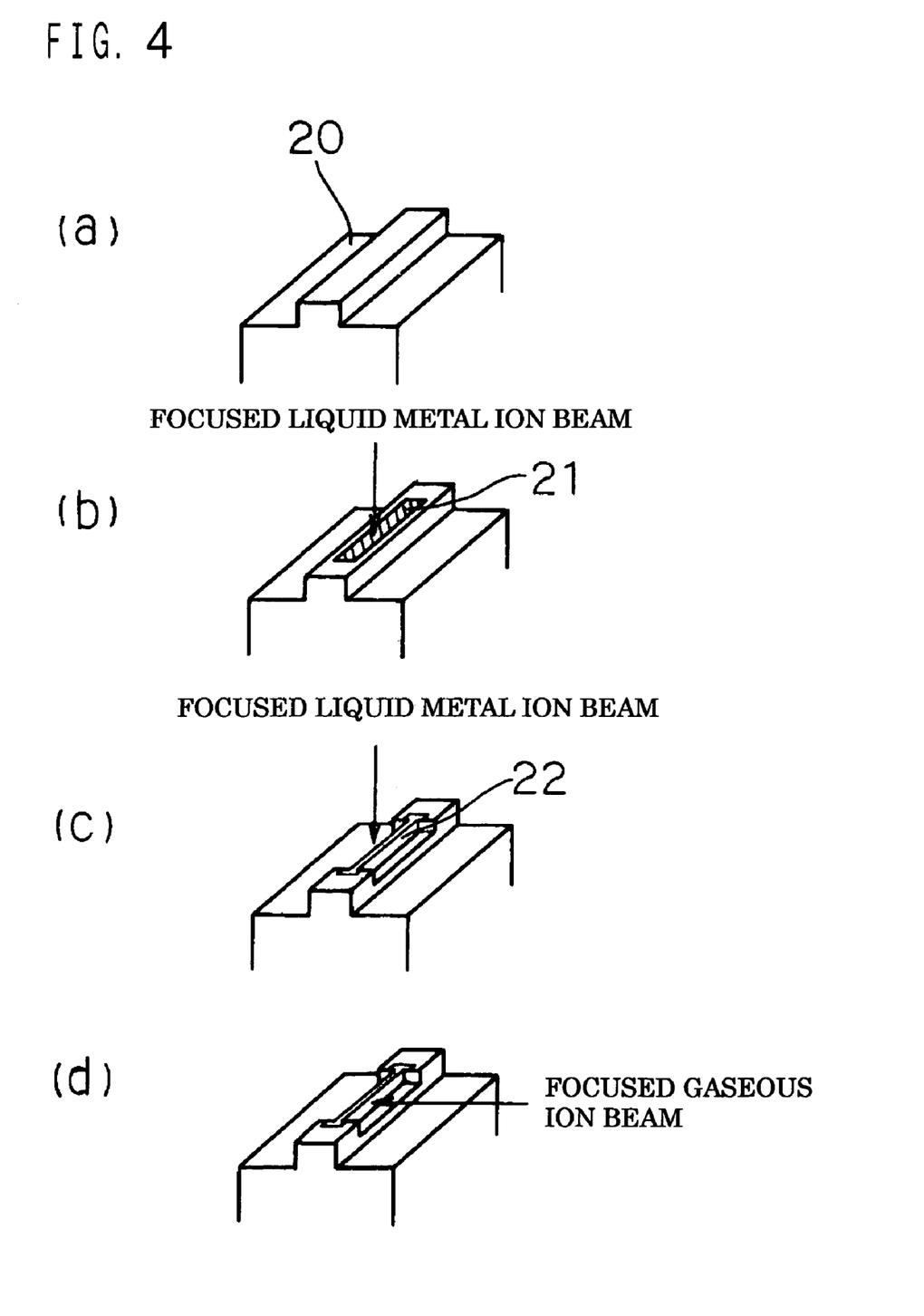

A portion containing a specific location (defect portion) of the wafer constituted by the sample 6 is subjected to preliminary processing by cutting with a dicing saw, and a cuspid-shaped small sample 20 having a cross section as shown in FIG. 4(a) is formed. The surface of the projecting section of the small sample 20 is the surface of the wafer, and in subsequent description the surface of this projection is referred to as the small sample 20.

The small sample 20 is supported at an existing support member, this is fixed by clamping to the sample holder 4 and is then carried onto the sample stage 5. The position and tilt angle of the sample stage 5 are adjusted in such a manner that the focused liquid metal ion beam from the liquid metal ion beam irradiation device 1 is incident in a substantially vertical manner with respect to the surface of the small sample 20.

Continuing on, prescribed gas is blown onto the surface of the small sample 20 using the gas gun 3, and a deposition film (protective film) 21 shown in FIG. 4(b) is formed by scanning a region containing the processing region of the surface of the small sample 20 using the focused liquid metal ion beam.

The processing region of the surface of the small sample 20 is then scanned using the focused liquid metal ion beam. The liquid metal ion beam is irradiated so as to be perpendicular with respect to the surface of the small sample 20. The surface of the region irradiated with the liquid metal ion beam is therefore gradually removed until finally the cross section 22 shown in FIG. 4(c) is obtained. The cross section 22 is the projection section of the small sample 20 shaved away from both sides, and the thickness is in the order of 0.1 to 0.5 μm.

Finally, the tilt angle of the sample stage 5 is adjusted in such a manner that the focused gaseous ion beam from the gaseous ion beam irradiation device 7 is incident in a substantially perpendicular manner with respect to the cross section 22 so that by then scanning a prescribed region (TEM scanning region) of the cross section 22 using the gaseous ion beam, the damaged layer formed during cross section processing using the liquid metal ion beam on the TEM observation region is removed by etching (FIG. 4(d)). Similar processing is then carried out for the cross section on the opposite side. Irradiation of a gaseous ion beam to the cross section on the opposite side can be carried out by rotating the sample stage 5 through 180 degrees.

In this embodiment, the observation region is positioned in the center of the cross section 22 and therefore is not next to the neighboring surfaces (bottom surface and side wall surface) neighboring the cross section 22. The focused gaseous ion beam therefore only irradiates the observation region during elimination of the damaged layer by etching in the same way as the case for picking up described above and neighboring surfaces are therefore not irradiated. Because of this, at the neighboring surface, emission of secondary particles due to irradiation with a gaseous ion beam as in the related art does not occur. Accordingly, forming of a reattachment layer due to secondary particles from the neighboring surface as in the related art at the surface of the observation region for which the damaged layer is removed does not occur.

Further, in this example, as with the case for picking up described above, if spot size occurring on a cross section 6a of the focused gaseous ion beam is set to be larger (but smaller than the cross section 22), it is possible to eliminate the damaged layer in a shorter period of time.

Elimination of the damaged layer by the focused gaseous ion beam in the pick up method and the method of manufacturing a TEM sample employing a small sample described above may be applied to manufacture of an SEM sample. In the case of an SEM sample, for example, a cross section is formed by making a concave-shaped hole using a liquid metal ion beam in a specific location for the wafer, and a damaged layer is removed by scanning a prescribed region (region to be monitored by the SEM) of the cross section using a focused gaseous ion beam. Further, in the case of making a small sample, a cross section is formed only at one surface of the small sample using a liquid metal ion beam, and a damaged layer is removed by scanning a prescribed region (region to be monitored by the SEM) of the cross section using a focused gaseous ion beam.

However, it is well known that streaks occur in the cross section during cross section processing by the liquid metal ion beam and damage layer elimination using the gaseous ion beam. For example, in the event that cross section processing is carried out on a sample having an uneven surface through irradiation of a liquid metal ion beam in a direction substantially perpendicular to the surface of the sample, a streak corresponding to the unevenness of the surface of the formed cross section occurs because the processing speed (etching speed) is different at the boundary (angle) of the uneven section and the flat portion. Further, in cases where regions (boundaries) of different materials exist, streaks occur due to differences in processing speed (etching speed) occurring at these regions. This kind of streaking is a hindrance to making superior cross section observations using the TEM and SEM.

With the FIB device of this embodiment, it is possible to remove the streaks described above by adopting either one of procedures 1 and 2 described in the following so as to enable superior cross section observation.

Procedure 1

(1-1) The focused liquid metal ion beam is irradiated onto the sample surface from a first direction of irradiation (for example, a direction perpendicular to the sample surface) and cross section processing is carried out. Streaking occurs during this cross section processing.

(1-2) In order to remove the streaks, the cross section obtained by the aforementioned cross section processing is irradiated and etched using a focused liquid metal ion beam from a second irradiation direction different to the first irradiation direction. As a result, the streaks formed on the cross section are removed.

(1-3) The cross section with the streaks removed is then irradiated with a focused gaseous ion beam from a third direction of irradiation so as to eliminate the damaged layer on the observation region of the cross section. Streaks are then formed in the damaged layer elimination process.

(1-4) The cross section obtained by the aforementioned cross section processing is irradiated and etched using a focused liquid metal ion beam from a second irradiation direction different to the first irradiation direction. As a result, the streaks formed on the cross section are removed.

The process described above in (1-1) and the process of (1-2) are carried out at the same time. Namely, cross sectional processing may be carried out by switching over the first irradiation direction and the second irradiation direction. Similarly, the process described above in (1-3) and the process of (1-4) are carried out at the same time. In this event, the damaged layer is eliminated by switching over between a third irradiation direction and a fourth irradiation direction.

Procedure 2

(2-1) The focused liquid metal ion beam is irradiated onto the sample surface from a first direction of irradiation (for example, a direction perpendicular to the sample surface) and cross section processing is carried out. Streaking occurs during this cross section processing.

(2-2) The cross section obtained by the aforementioned cross section processing is irradiated so as to eliminate the damaged layer on the cross section using a focused gaseous metal ion beam from a second irradiation direction different to the first irradiation direction. In the damaged layer elimination process, streaks caused in (2-1) are eliminated by new streaks are formed on the cross section due to irradiation with a gaseous ion beam.

(2-3) The cross section obtained by the cross section processing of (2-) is irradiated and etched using a focused liquid metal ion beam from a second irradiation direction different to the first irradiation direction. As a result, the streaks formed on the cross section are removed.

The process described above in (2-2) and the process of (2-3) are carried out at the same time. Namely, damaged layer elimination may be carried out by switching over the second irradiation direction and the third irradiation direction. In this event, streaks caused at the time of processing the cross section and streaks caused during elimination of the damaged layer are eliminated at the same time.

Switching of the direction of irradiation occurring in procedure 1 and procedure 2 can be carried out by controlling the tilt angle of the sample stage.

The FIB device described above is merely given as an example, and the device configuration and processing procedures are not limited to those shown in the drawings, with appropriate modifications being possible. For example, it is possible to incorporate devices for monitoring use such as an SEM or TEM etc. and manipulators etc. in the FIB device.

Figure 1:
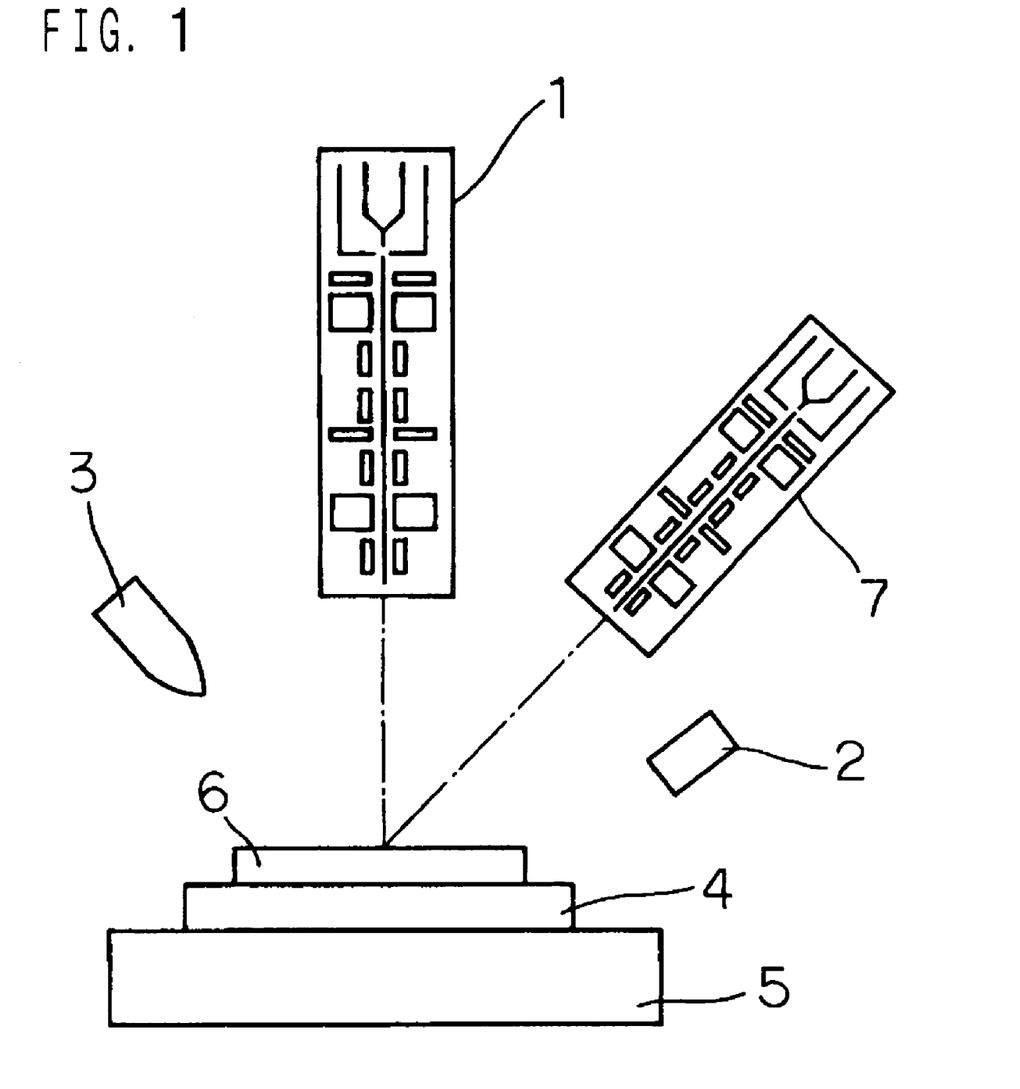
FIG. 1 is a block view showing the main parts of a configuration for an FIB device constituting an embodiment of the present invention.
Figure 5:
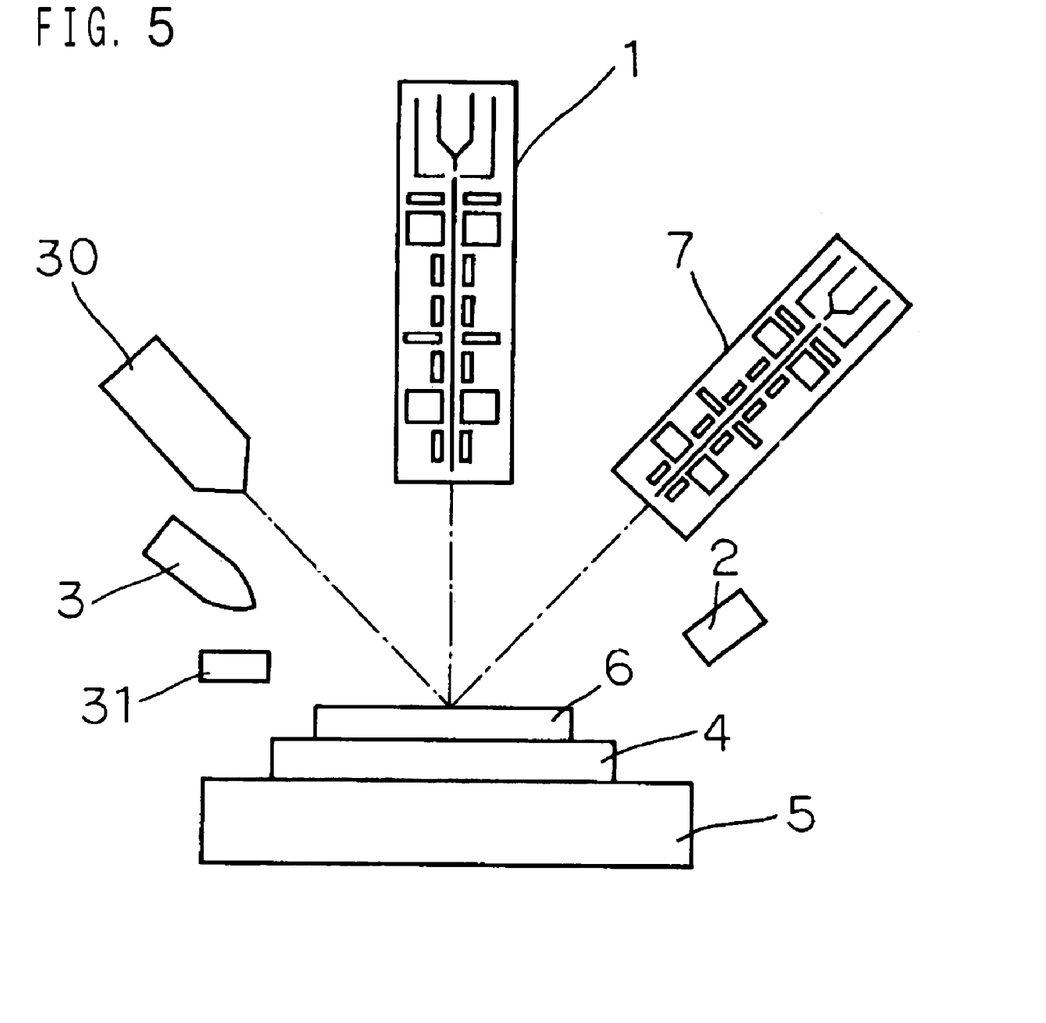

An outline of a configuration for a composite device where a function enabling cross section observation by an SEM is incorporated in the FIB device shown in FIG. 1 is shown in FIG. 5. In the configuration shown in FIG. 1, the composite device is comprised of an electron beam irradiation device 30 for scanning a cross section formed on a sample 6 using an electron beam, and a secondary electron detector 31 for detecting secondary electrons emitted form the cross section occurring due to scanning by the electron beam.

In the event that a cross section formed at specific portions of the sample 6 is monitored with an SEM, tilt angle of the sample stage 5 is controlled in such a manner that an electron beam from the electron beam irradiation device 30 is incident to the cross section at a prescribed angle. The cross section is then scanned by an electron beam, and secondary electrons emitted from the cross section as a result of the scanning are detected by the secondary electron detector 8. An SEM image is obtained based on the output of this secondary electron detector 8.

In the ion beam device of the present invention described above, the acceleration voltage of the gaseous ion beam is typically 10V to 10 kV but is preferably low to ensure that there is little damage. However, when a low acceleration voltage is adopted, the etching speed becomes slow and it is therefore preferable to set the acceleration voltage to complete etching within a practical time.

Further, the focused gaseous ion beam is incident in a substantially perpendicular manner or at an angle with respect to the cross section but the present invention is by no means limited in this respect. For example, if it is the case that cross section processing is implemented by irradiating the surface of a sample with a liquid metal ion beam coming from a normal direction, it is possible to remove a damaged layer on a prescribed region (TEM observation region or SEM observation region) of the cross section through irradiation with a focused gaseous ion beam from the same normal direction. In this event, part of the gaseous ion beam irradiates the neighboring surface (bottom surface) and secondary particles are emitted. The extent of these emissions is quite small compared to the extent of emissions of secondary particles at neighboring surfaces in the related art. As a result, even if a reattachment layer is formed at the portion for which the damaged layer is eliminated, this amount (thickness) is only slight and cross section observation is therefore not impeded.

Field of Industrial Utilization

As described above, according to the present invention, a reattachment layer of secondary particles from surfaces neighboring an observation surface (cross section) is not formed when eliminating a damaged layer. It is therefore possible to carry out superior cross section observations with SEMs and TEMs and provide TEM samples and SEM samples.

The invention claimed is:

1. An ion beam device comprising:
   liquid metal ion beam irradiation means for irradiating a specific portion of a sample with a prescribed liquid metal ion beam so as to form a cross section of the sample; and
   gaseous ion beam irradiation means for scanning a prescribed region of the cross section using a gaseous ion beam focused to a prescribed diameter smaller than the size of the cross section and removing a damaged layer on the prescribed region.

2. An ion beam device according to claim 1; wherein the prescribed diameter of the gaseous ion beam on the cross section is smaller than the size of the prescribed region.

3. An ion beam device according to claim 1; wherein the gaseous ion beam irradiation means is configured in such a manner that the gaseous ion beam is incident in either a substantially perpendicular manner or at an incline with respect to the cross section.

4. An ion beam device according to claim 1; wherein the gaseous ion beam is an inert gas ion beam.

5. An ion beam device according to claim 1; further comprising in combination therewith an electron microscope for scanning the prescribed region using an electron beam and forming a transmitted electron image or secondary electron image for the prescribed region.

6. An ion beam device according to claim 1; wherein the cross section is a cross section of a TEM sample.

7. An ion beam device according to claim 1; wherein the cross section is a cross section of a SEM sample.

8. An ion beam device according to claim 1; wherein the liquid metal ion beam irradiation means is a focused liquid metal ion beam device.

9. An ion beam device according to claim 1; wherein the sample is a wafer.

10. An ion beam processing method comprising:
    a first step of irradiating a specific portion of a sample with a prescribed liquid metal ion beam to form a cross section of the sample; and
    a second step of scanning a prescribed region of the cross section using a gaseous ion beam focused to a prescribed diameter smaller than the size of the. cross section and removing a damaged layer on the prescribed region.

11. An ion beam processing method according to claim 10; wherein the second step includes a step of changing the angle of incidence of the gaseous ion beam to the cross section so as to eliminate the damaged layer.

12. An ion beam processing method according to claim 11; wherein the first step includes a step of changing an angle of irradiation of the prescribed liquid metal ion beam so as to form a cross section.

13. An ion beam processing method according to claim 10; wherein the prescribed diameter of the gaseous ion beam on the cross section is smaller than the size of the prescribed region.

14. An ion beam processing method according to claim 13; wherein the gaseous ion beam is an inert gas ion beam.

15. An ion beam processing method according to claim 10; wherein the gaseous ion beam is an inert gas ion beam.

16. An ion beam processing method according to claim 10; wherein the first step includes a step of changing an angle of irradiation of the prescribed liquid metal ion beam so as to form a cross section.

17. An ion beam processing method according to claim 10; wherein the cross section is a cross section of a TEM sample.

18. An ion beam device according to claim 10; wherein the cross section is a cross section of a SEN sample.

19. An ion beam processing method according to claim 10; wherein the sample is a wafer.

* * * * *